United States Patent [19]

Mechalas et al.

[11] Patent Number: 4,940,902
[45] Date of Patent: Jul. 10, 1990

[54] APPARATUS AND METHOD FOR CONTINUOUS MEASUREMENT OF SUSPENDED SOLIDS IN A LIQUID MEDIUM WITH WIPING MEANS

[76] Inventors: Emmanuel Mechalas, 2830 Townway, Danville, Ill. 61832; Laverne E. Foran, 240 S. Park Rd., La Grange, Ill. 60525

[21] Appl. No.: 261,754

[22] Filed: Oct. 24, 1988

[51] Int. Cl.⁵ ............................................. G01N 15/06
[52] U.S. Cl. .................................. 250/573; 250/227.25
[58] Field of Search ............... 250/227, 573, 574, 575; 356/441, 442, 440

[56] References Cited

U.S. PATENT DOCUMENTS 4,740,709  4/1988  Leighton et al. ...................... 250/573

Primary Examiner—David C. Nelms
Attorney, Agent, or Firm—Neal J. Mosely

[57] ABSTRACT

An apparatus and method continuously samples and measures the changing concentration and/or density of suspended solids in a liquid medium without electrical connections at the submerged points in the liquid. A submersible sensing head is connected by an elongate probe to an non-submersible enclosure which contains at least one light source and one light detector. The sensing head has an apertured sample chamber allowing liquid to flow freely therethrough when submerged and contains at least one light emitting lens and at least one light receiving lens aligned in the flow path. The light emitting lens is connected to the light source and the light receiving lens is connected to the light detector with fiber optic bundles extending the probe. An elongate shaft extends through the probe and into the sensing head sample chamber and has a lens wiper at its lower end. The shaft is reciprocated by a timed motor in the enclosure to move the lens wiper between the lenses to wipe them clean of debris at selective continuous or intermittent cycles. When the sensing head is submerged light is transmitted from the light source to the emitting lens through the liquid between the lenses to the receiving lens and to the light detector for determining the concentration and/or density of suspended solids in the sample liquid with no submerged electrical connections.

13 Claims, 1 Drawing Sheet

APPARATUS AND METHOD FOR CONTINUOUS MEASUREMENT OF SUSPENDED SOLIDS IN A LIQUID MEDIUM WITH WIPING MEANS

BACKGROUND OF THE INVENTION

FIELD OF THE INVENTION

This invention relates generally to measuring apparatus and methods, and more particularly to an apparatus and method utilizing fiber optics for continuously measuring suspended solids in a liquid medium and has no electrical connections at the submerged points in the liquid.

BRIEF DESCRIPTION OF THE PRIOR ART

Devices are known which employ a light source submerged in a liquid and are designed to direct a beam of light through the liquid to a submerged light receiver for the purpose of "on stream" continuous measurement of the amount of solids suspended in the liquid and/or detect (locate) the interface, or dividing line between solids of high and low densities within a liquid. Interface devices are known as Sludge Blanket Detectors. Suspended Solids devices are known as Suspended Solids Analyzers or Meters. When employing light beams, they are known as "Optical" or "Light Transmittance" devices.

There are several patents which disclose various types of optical or light transmittance devices utilizing light beams to analyze the condition of a liquid.

Topal et al, U.S. Pat. No. 4,451,152 discloses a submerged sensing head with a reciprocating piston connected to a non-submerged motor and to which a combination "wiper-seal" is attached to draw periodic samples of the liquid into a sample chamber fitted with a transparent liner where the liquid is exposed to the light beam and photocells located on the outside of the liner. The sample is then expelled by the outward stroke of the reciprocating piston while mechanically wiping the inner surface of the sample chamber liner at the same time. The transparent liner is required to isolate the electrical connections to the lamps and photocells from the liquid.

Other types of liquid analyzers utilizing light beams, such as U.S. Pat. No. 4,114,038 assemble a motor and sensing probes in a single unit and submerge the entire assembly, including the motor into the liquid. The motor is used to periodically move the sensing probes in and out of the body of the assembly where wiping devices clean the probes during the in and out motion.

Still other types, which do not have the feature of mechanical cleaning of the optics, simply immerse the optical components in the liquid and depend on stream velocity and/or "electronic compensation" to keep the optic clean.

A major problem with devices which require electrical connections to submerged lights and light receivers is the frequent and expensive replacement of light components (lamps and photocells) due to moisture shorting the circuits and burning out the components despite attempts to isolate the electrical connections from moisture through the use of liners, O-rings, and other sealing means. The unpredictability chamber fitted with a transparent liner where the liquid is exposed to the light beam and photocells located on the outside of the liner. The sample is then expelled by the outward stroke of the reciprocating piston while mechanically wiping the inner surface of the sample chamber liner at the same time. The transparent liner is required to isolate the electrical connections to the lamps and photocells from the liquid.

Other types of liquid analyzers utilizing light beams, such as U.S. Pat. No. 4,114,038 assemble a motor and sensing probes in a single unit and submerge the entire assembly, including the motor into the liquid. The motor is used to periodically move the sensing probes in and out of the body of the assembly where wiping devices clean the probes during the in and out motion.

Still other types, which do not have the feature of mechanical cleaning of the optics, simply immerse the optical components in the liquid and depend on stream velocity and/or "electronic compensation" to keep the optic clean.

A major problem with devices which require electrical connections to submerged lights and light receivers is the frequent and expensive replacement of light components (lamps and photocells) due to moisture shorting the circuits and burning out the components despite attempts to isolate the electrical connections from moisture through the use of liners, O-rings, and other sealing means. The unpredictability of the occurrence of moisture induced shorting makes it difficult or impossible to deliver the continuous accurate signals needed for computerized automatic control systems.

When liners are needed in the sample chambers these types of devices to isolate electrical connections from the liquid, "O" rings or other types of seals must be provided between the outside of the liner and the wall of the sample chamber to prevent leakage through that area which would reach the electrical connections. The reciprocating wiper must fit tight inside the liner to seal against water escaping past the wiper and reaching the electrical connections to the photocells and lamps. Despite these preventive measures, moisture penetrates to these connections and causes short circuiting. The result is frequent and high maintenance costs.

Another problem with piston/sensing head types of devices is that they require the reciprocating action to be continuous even though continuous cleaning may not be necessary. The need for continuous reciprocation causes rapid wear of parts which together with shorting of submerged electrical connections results in frequent and unnecessarily high maintenance costs and "down" time of the equipment.

It would therefore be desirable to provide a device capable of continuous, "on stream" measurement of suspended solids (as opposed to laboratory bench testing) in a liquid and which is capable of detecting (locating) the interface, or dividing line between solids of high and low densities within a liquid, commonly known as the "Sludge Blanket Level," by submerging one or more light emitters and one or more light receivers in a liquid and passing a beam of light from the emitter through the liquid to the receiver and thence to a non-submerged remote readout device without the need for submerged electrical connections to the light emitter and receiver and therefore without the need for a transparent liner in the sample chamber of the sensing head to isolate electrically connected optical components (lamps and photocells) from the liquid.

The present invention is distinguished over the prior art in general, and these patents in particular by an apparatus and method for continuous sampling and measuring of the changing concentration and/or density of suspended solids in a liquid medium without electrical connections at the submerged points in the liquid. The present invention utilizes a submersible sensing head connected by an elongate probe to an non-submersible enclosure which contains at least one light source and one light detector. The sensing head has an apertured sample chamber to allow liquid to flow freely therethrough when submerged and contains at least one light emitting lens and at least one light receiving lens aligned therewith in the flow path such that the liquid flows therebetween. The light emitting lens is connected to the light source and the light receiving lens is connected to the light detector with fiber optic bundles which extend through the probe. An elongate shaft extends through the probe and into the sensing head sample chamber and has a lens wiper at its lower end. The shaft is reciprocated by a timed motor in the enclosure to move the lens wiper between the lenses to wipe them clean of debris at selective continuous or intermittent cycles. When the sensing head is submerged light is transmitted from the light source to the emitting lens, through the liquid between the lenses to the receiving lens, and to the light detector for determining the concentration and/or density of suspended solids in the sample liquid with no submerged electrical connections.

SUMMARY OF THE INVENTION

It is therefore an object of the present invention to provide an apparatus and method utilizing fiber optics for measuring suspended solids in a liquid medium which is capable of continuous, "on stream" measurement and analysis (as opposed to bench testing) to accurately reflect and measure the changing concentration of suspended solids in a liquid.

It is another object of this invention is to provide an apparatus and method utilizing fiber optics which is capable of detecting the interface, or dividing line between solids of high and low densities within a liquid, commonly known as the "Sludge Blanket Level" without submersed electrical connections.

Another object of this invention is to provide an apparatus and method utilizing fiber optics for measurement and analysis of suspended solids in a moving or stationary liquid medium in which there are no submerged electrical connections to the light emitting means and light receiving means.

Another object of this invention is to provide an apparatus and method utilizing fiber optics for measurement and analysis of suspended solids in a liquid medium which does not require a transparent liner in the sensing head sample chamber to isolate the electrically connected optical components, such as lamps and photocells, from the liquid.

Another object of this invention is to provide an apparatus and method utilizing fiber optics for measurement and analysis of suspended solids in a liquid medium which does not require a combination "wiper/seal" or continuous reciprocation and utilizes vent ducts in the sensing head which produces a continuous flow of liquid through the sample chamber and keeps the moving liquid exposed to the light emitting and receiving means at all times when immersed in the liquid.

A further object of this invention is to provide an apparatus and method utilizing fiber optics for measurement and analysis of suspended solids in a moving or stationary liquid medium wherein cleaning of the optic components may be intermittent or continuous as determined by a re-cycling timing means.

A still further object of this invention is to provide an apparatus utilizing fiber optics for measurement and analysis of suspended solids in a moving or stationary liquid medium which is simple in design, economical to manufacture, rugged and reliable in operation, and free of malfunctions caused by short circuiting of submerged electrical connections.

Other objects of the invention will become apparent from time to time throughout the specification and claims as hereinafter related.

The above noted objects and other objects of the invention are accomplished by the apparatus and method for continuous sampling and measuring of the changing concentration and/or density of suspended solids in a liquid medium without electrical connections at the submerged points in the liquid which comprises a submersible sensing head connected by an elongate probe to an non-submersible enclosure which contains at least one light source and one light detector. The sensing head has an apertured sample chamber to allow liquid to flow freely therethrough when submerged and contains at least one light emitting lens and at least one light receiving lens aligned therewith in the flow path such that the liquid flows therebetween. The light emitting lens is connected to the light source and the light receiving lens is connected to the light detector with fiber optic bundles which extend through the probe. An elongate shaft extends through the probe and into the sensing head sample chamber and has a lens wiper at its lower end. The shaft is reciprocated by a motor in the enclosure to move the lens wiper up and down between the lenses to wipe them clean of debris at selective continuous or intermittent cycles. When the sensing head is submerged light is transmitted from the light source to the emitting lens, through the liquid between the lenses to the receiving lens, and to the light detector for determining the concentration and/or density of suspended solids in the sample liquid with no submerged electrical connections.

DESCRIPTION OF THE PREFERRED EMBODIMENT

Figure 1:
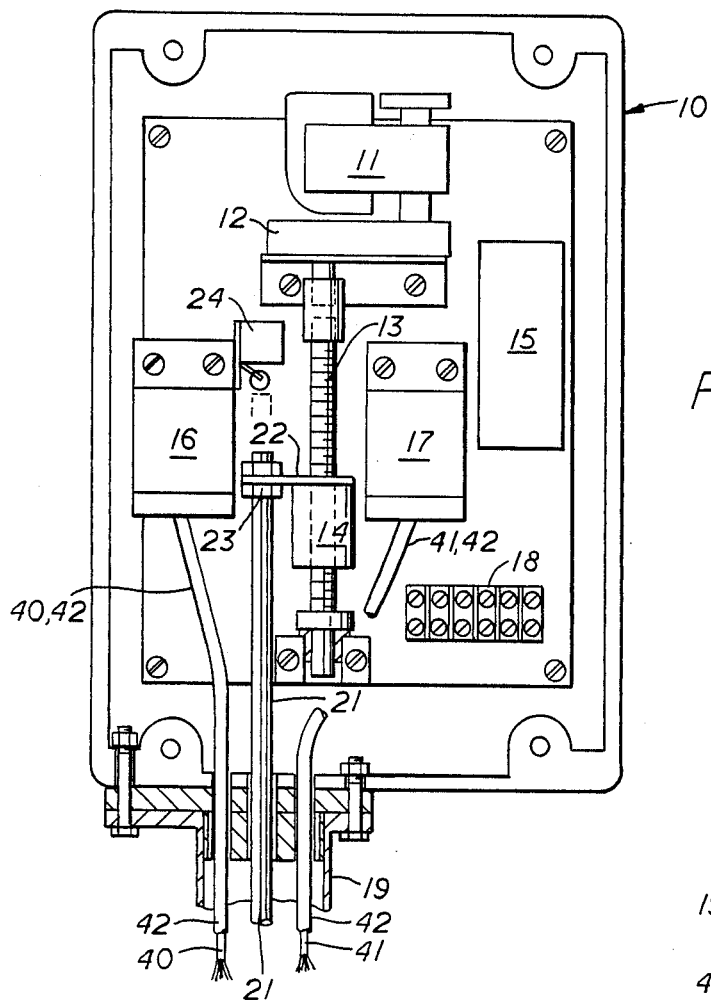
FIG. 1 is an elevation, with cover removed, of the control box of the present fiber optic system for measurement and analysis of suspended solids in a liquid medium.

Referring to the drawings by numerals of reference, the preferred fiber optic sensing apparatus comprises the components shown in FIGS. 1, 2, 3, and 4 together with an indicator or read-out dial (not shown) mounted in the control box or in a separate enclosure connected to the control box by an electric cable.

Referring now to FIG. 1, a weatherproof enclosure or control box 10 houses a drive motor 11 having its output shaft connected through a gear box 12 to a threaded shaft 13 rotatably journaled at its bottom end in the control box. A traveling ball reverser 14 rides up and down on shaft 13 as it rotates. A recycling timer 15 connected to motor 11 governs the operation of the motor. One or more light sources or emitter blocks 16 and light detectors or receiver blocks 17 and an electrical terminal board 18 are mounted in control box 10.

An elongate hollow tubular probe 19 of suitable material is secured by conventional means such as bolting, to the bottom of control box 10. A cylindrical sensing head 20 (described below) is secured to the bottom end of probe 19. An elongate shaft 21 is connected near its upper end to ball reverser 14 by a rigid link 22 and retaining collars 23 and extends through the center of probe 19 into sensing head 20. A micro switch 24 is mounted above the top end of shaft 21.

Figure 2:
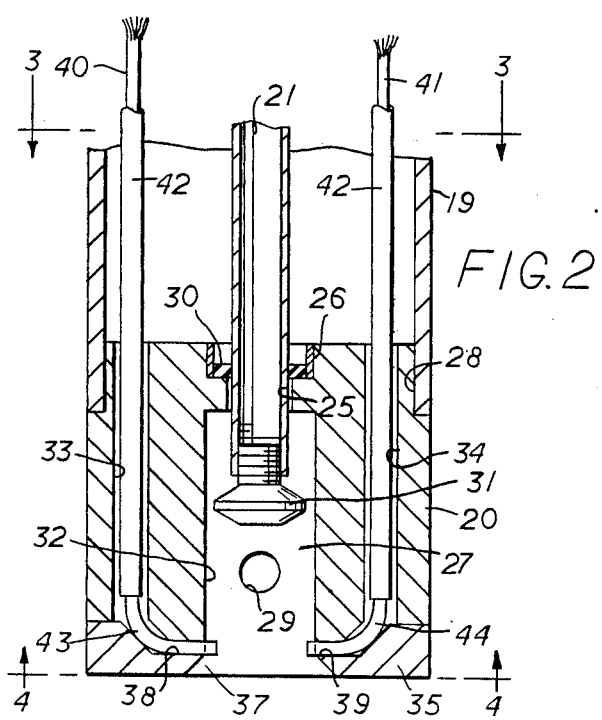
FIG. 2 is a partial sectional view of a preferred fiber optic sensing head apparatus in accordance with the present invention.
Figure 3:
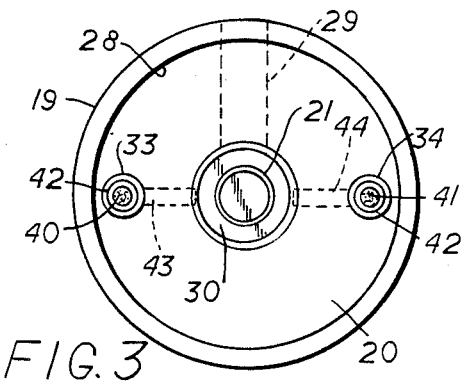
FIG. 3 is top plan view of the sensing head shown in FIG. 2.
Figure 4:
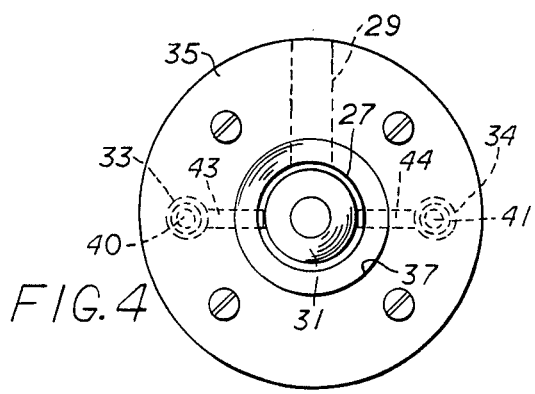
FIG. 4 is a bottom plan view of the sensing head shown in FIG. 2.

As shown in FIGS. 2, 3, and 4, sensing head 20 is a cylindrical member having a central bore 25 with a counter bore 26 at the top end and an elongate counterbore at the bottom end terminating beneath the central bore to define a sample chamber 27. The exterior diameter of sensing head 20 is approximately the same as the exterior diameter of probe 19 and its upper portion has a reduced diameter 28 which is slidably received in and secured to the bottom of the probe by conventional means. One or more apertures or vent ducts 29 extend through the side wall of sensing head 2 to establish fluid communication between the sample chamber 27 and the exterior of the sensing head.

The lower end of shaft 21 is received within sample chamber 27, and a fluid seal 30 installed in counterbore 26 surrounds the shaft to provide a fluid tight seal between the shaft and the chamber. A disk-shaped elastomeric lens wiper 31 is secured to the bottom end of shaft 21. Because there are no electrical connections in the sensing head 20, the lens wiper 31 does not have to act as a "seal" between sample chamber wall 32 and wiper 31 may be a loose fit as shown in FIG. 2. Wiper 31 may be of any suitable material and configuration necessary for its wiping (cleaning) function. The length of probe 19 and shaft 21 may be varied to suit the particular installation requirements.

A pair of longitudinal bores 33 and 34 spaced radially from sample chamber 27 extend through cylindrical sensing head 20. An end cap 35 is secured to the bottom of sensing head 20 by screws 36 or other conventional means and has a central bore 37 coaxial with the sample chamber. A pair of opposed bores 38 and 39 extend radially inward from each longitudinal bore 33-34 to the interior of sampling chamber 27 along the joint between the sensing head bottom and end cap 35. It should be noted that bottom opening or bore 37 and vent ducts 29 provide a fluid flow path through sample chamber 27 when sensing head 20 is submerged.

Fiber optic bundles 40 and 41 enclosed in waterproof flexible cables 42 are connected at their upper end to light emitter box 16 and light receiver box 17 respectively are routed through the inside of probe 19 and through longitudinal bores 33 and 34 in sensing head 20. A light emitting lens 43 is installed in bore 38 with its upper end connected to fiber optic bundle 40 and a light receiving lens 44 is installed in opposed bore 39 and connected at it upper end to fiber optic bundle 41. The lower ends of the lenses 43 and 44 terminate a short distance inwardly from interior wall 32 of sample chamber 27 in diametrically opposed relation. Thus, the face of lenses 43 and 44 are directly exposed in the fluid flow path between bottom opening 37 and vent ducts 29.

Fiber optic bundle 40 receives light from light emitter block 16 and conveys it to light emitter lens 43 in sensing head 20. Light receiving lens 44 receives light from emitter lens 43 and conveys it through fiber optic bundle 41 to light receiver block 17 which converts the change in light intensity (input at emitter block minus input at receiver block) to a read-out on an indicator (not shown) in the desired units such as; parts per million, percent solids or other.

OPERATION

The end of probe 19 and sensing head 20 are immersed in the liquid to be analyzed. As motor 11 drives ball reverser 14 and rigid link 22 up and down on threaded shaft 13, elongate shaft 21 and attached lens wiper 31 are driven in a reciprocating motion. The position of shaft 21 is adjustable by means of retaining collars 23 so that when the shaft is at the lowest point of its stroke, lens wiper 31 will have frictionally passed and completely cleaned the protruding ends of light emitting and receiving lenses 43 and 44.

Vent ducts 29 passing from the outside surface of sensing head 20, through its side wall and into sample chamber 27 ensures a continuous flow of liquid through the sample chamber so that the changing densities of solids in the flowing stream will be accurately recorded even when the cleansing action is in the intermittent mode, as pre-set on recycling timer 15, and the reciprocating action of lens wiper 31 is at rest. Without vent ducts 29 to vent sample chamber 27 to the outside, an air pocket would form in the upper portion of the sample chamber which would result in a partially filled chamber. The partial sample would become stagnant, the solids would settle out and the sample would not be representative of the flowing stream.

As mentioned previously, conventional mechanical self-cleaning instruments using submerged optical components (lights and photocells) must use a transparent liner in the sample chamber to isolate the electrical connections to those components from the liquid in order to avoid short circuiting and thus cannot vent the sample chamber with ducts as the present invention does. Consequently, they are forced to use continuous reciprocation of the piston and wiper seal to "suck in" fresh samples and expel them in order to ensure that the sample being analyzed is representative of the flowing stream.

As ball reverser 14 reverses its direction and wiper equipped shaft 21 begins its upward stroke, lens wiper 31 again cleans light emitting and receiving lenses 43 and 44. As the upward stroke continues, the liquid which flowed into sample chamber 27 through vent ducts 29 on the downward stroke is expelled back through the ducts and back into the flowing stream from whence it came while a new, fresh sample flows into the sample chamber through end opening 39. The length of the stroke is designed so that when a cleaning cycle (one down and up stroke) is completed, shaft 21 is at the top of its stroke and trips micro switch 24 which shuts off motor 11 with lens wiper 31 at rest above vent ducts 29 thus permitting the liquid to flow unrestricted through sample chamber 27 so that the analysis will correctly represent the changing density of solids in the moving stream. When the frequency setting on recycling timer 15 is timed out, motor 11 is re-energized and a new cleaning cycle is started. The frequency of cycles is adjustable to provide continuous or intermittent cleaning of fiber optic lenses 43 and 44.

To accomplish the measurement of suspended solids, one or more light sources of known intensity, located in the emitter block(s) 16, is directed into the fiber optic bundle 40 encased in waterproof flexible cable 42. The cables and fiber optic bundles are routed through hollow probe 19. The fiber optic bundles terminate at emitting lenses 43 strategically located on the inner surface of sample chamber wall 32 in sensing head 20. When sensing head 20 is immersed in a liquid, sampling chamber 27 is filled and the light emitted from fiber optic emitting lenses 43 penetrates the liquid without the need of submerged electrical connections.

The solids suspended in the liquid, the quantity of which the device is to measure, causes some of the light to be absorbed, some to be scattered, some diffused, and some passes straight through the liquid. In order to determine the change in light intensity from the known light source intensity, and caused by the solids suspended in the liquid, one or more fiber optic receiving lenses 44 are placed at strategic positions around the inner surface of the sampling chamber wall 32. The amount of light received by each of fiber optic receiving lenses 44 is transmitted through fiber optic receiving bundles 41 to receiver block(s) 17.

The resultant change in light intensity from the known source intensity is electronically measured and converted within receiver block 17 into quantitative units such as parts per million (ppm), percent (%) solids or other desired units. The measurements are the conveyed to visual indicator dials or to computer processing equipment (not shown). The delivery of the light from emitter block(s) 16 to submerged fiber optic emitter lenses 43 in sampling chamber 27 and the pick-up and delivery of the light received by each of fiber optic receiving lenses 44 to receiver blocks 17 is all accomplished with no submerged electrical conductors or connections. All necessary electrical wiring is contained in weatherproof enclosure or control box 10.

Vent ducts 29 are positioned above the emitting and receiving lenses 43 and 44 which provides "double entry" to sample chamber 27, i.e. through end opening 37 and vent ducts 29 to produce a continuous flow of liquid through sample chamber 27 identical to that of the moving stream being analyzed so that the analyzer is, in effect, "seeing" the continuously changing densities of solids in the moving stream. Further, because there are no electrical connections in sensing head 20, lens wiper 31 does not have to act as a "seal" between sample chamber wall 32 and the wiper.

Thus, the present apparatus and method eliminates the need of an isolating liner in the sampling chamber, a tight fitting wiper-seal, and the need for continuous reciprocation of the piston and wiper seal, and makes it possible to transmit light from a non-submerged source to a submerged source without the need for electrical connections at the submerged positions of light emitters and receivers.

While this invention has been described fully and completely with special emphasis upon a preferred embodiment, it should be understood that within the scope of the appended claims the invention may be practiced otherwise than as specifically described herein.

We claim:

1. A method of continuously sampling and measuring the concentration of suspended solids in a liquid medium comprising the steps of
   providing a submersible sample chamber which is apertured to allow liquid to flow freely therethrough and has at least one light emitting lens in the liquid flow path connected by a fiber optic bundle to a non-submerged light source and at least one light receiving lens in the liquid flow path aligned with the emitting lens and connected by a fiber optic bundle to a non-submerged light detector with no electrical connection in the submersible portion,
   submitting the apertured sample chamber in the liquid medium to be sampled and measured to allow continuous fluid communication between the interior and exterior of the sample chamber through the liquid flow path and between the light emitting and light receiving lenses therein, and
   transmitting light from the non-submerged light source to the emitting lens, through the liquid between the lenses to the light receiving lens, and from the receiving lens to the non-submerged light detector for determining the concentration and/or density of suspended solids in the sample liquid,
   providing a movable lens wiper in the sample chamber configured to contact the lens members sufficiently to wipe them clean of debris upon movement therebetween while allowing clearance between the sample chamber wall and in its stationary position allowing an unrestricted light and fluid flow path in the sample chamber, and
   moving the lens wiper between the lens members at selective continuous or intermittent cycles.

2. Apparatus for continuous sampling and measuring of the changing concentration and/or density of suspended solids in a liquid medium without electrical connections at the submerged points in the liquid, the apparatus comprising
   a non-submerged enclosure containing at least one light source and one light detector,
   a submersible sensing head remotely connected to said enclosure and adapted to be submerged in the liquid to be sampled and measured,
   said sensing head having an apertured sample chamber to allow liquid to flow freely therethrough when submerged,
   at least one light emitting lens and at least one light receiving lens aligned therewith in the flow path such that the liquid flows therebetween, and
   wiping means movable in wiping relation to said lens members to wipe said lens members at selective continuous or intermittent cycles,
   said light emitting lens being connected to the light source and said light receiving lens being connected to the light detector with fiber optic bundles, whereby
   when said sampling head is submerged light is transmitted from the non-submerged light source through the fiber optic bundle to the emitting lens, through the liquid between the lenses to the receiving lens, and through the fiber optic bundle to the non-submerged light detector for determining the concentration and/or density of suspended solids in the sample liquid with no submerged electrical connections.

3. Apparatus according to claim 2 in which
   said wiping means comprises a lens wiper mounted in said sample chamber and configured to contact said lens members sufficiently to wipe them clean of debris upon movement therebetween while allowing clearance between the sample chamber wall,
   said lens wiper in its stationary position disposed in said sample chamber relative to said lens members and said apertures to allow an unrestricted light and fluid flow path in the sampling chamber, and motor means operable to move said lens wiper between said lens members at selective continuous or intermittent cycles.

4. Apparatus according to claim 3 including
motor means contained in said enclosure,
an elongate shaft coupled at one end to said motive means and moved thereby and its other end extending into said sensing head sample chamber,
said lens wiper being mounted on the extended end of said shaft within said sample chamber and configured to contact said lens members sufficiently to wipe them clean of debris upon movement therebetween while allowing clearance between the sample chamber wall,
said lens wiper in its stationary position disposed in said sample chamber relative to said lens members and said apertures to allow an unrestricted light and fluid flow path in the sampling chamber, and
said motor means operable to move said lens wiper between said lens members at selective continuous or intermittent cycles.

5. Apparatus according to claim 4 including
timer means operatively connected to said motor means for moving said lens wiper at selective continuous or intermittent cycles.

6. Apparatus according to claim 4 in which
said motor means comprises a drive motor having its output shaft connected through a gear box to a threaded shaft rotatably journaled in said weatherproof enclosure,
a traveling ball reverser movably connected to said threaded shaft to ride up and down thereon as it rotates,
said elongate shaft coupled at one end to said ball reverser means for movement therewith and thereby moving said lens wiper at its other end within said sensing head sample chamber.

7. Apparatus according to claim 6 in which
said sensing head comprises a cylindrical member secured to one end of an elongate tubular probe and having a cylindrical sample chamber,
said probe secured at its other end to said enclosure,
said elongate shaft extending longitudinally through said probe and into the cylindrical sample chamber.

8. Apparatus according to claim 7 in which
said sensing head sample chamber has an open bottom end and said sensing head has one or more apertures extending transversely through its side wall to establish fluid communication between the sample chamber and the sensing head exterior.

9. Apparatus according to claim 7 in which
said lens wiper comprises a generally disk-shaped member mounted on the bottom end of said elongate shaft.

10. Apparatus according to claim 9 in which
said lens wiper is formed of elastomeric material.

11. Apparatus according to claim 7 in which
said sample chamber has a fluid seal at its upper end surrounding said elongate shaft to provide a fluid tight seal therebetween.

12. Apparatus according to claim 2 in which
said sensing head comprises a cylindrical member secured to one end of an elongate tubular probe and having a cylindrical sample chamber,
said sample chamber having an open bottom end and said sensing head having one or more apertures extending transversely through its side wall to establish fluid communication between the sample chamber and the sensing head exterior,
said probe secured at its other end to said weatherproof enclosure,
at least two longitudinal bores spaced radially from the sample chamber and extending into the sensing head and at their bottom end extending into the sample chamber in diametrically opposed relation.

13. Apparatus according to claim 12 in which
said light emitting lens is installed at the bottom of one said longitudinal bore with its upper end connected to said fiber optic bundle,
said light receiving lens is installed in bottom of the diametrically opposed bore and connected at it upper end to said the fiber optic bundle,
the lower end of each said lens terminating a short distance inwardly from the interior wall of the sample chamber in diametrically opposed relation to be directly exposed in the fluid flow path between said bottom opening and said apertures, and
said fiber optic bundles enclosed in waterproof flexible cables and routed through the inside of said probe and through said longitudinal bores in said sensing head.

* * * * *